United States Patent
Kim et al.

(10) Patent No.: US 9,636,080 B2
(45) Date of Patent: May 2, 2017

(54) SYSTEMS FOR MONITORING THE CARDIOVASCULAR SYSTEM USING A HEART LUNG SOUND

(71) Applicant: THE ASAN FOUNDATION, Seoul (KR)

(72) Inventors: Sung-Hoon Kim, Seoul (KR); Segyeong Joo, Seoul (KR); Gyu-Sam Hwang, Seoul (KR)

(73) Assignee: THE ASAN FOUNDATION, Seoul (KR)

( * ) Notice: Subject to any disclaimer, the term of this patent is extended or adjusted under 35 U.S.C. 154(b) by 0 days.

(21) Appl. No.: 14/814,951

(22) Filed: Jul. 31, 2015

(65) Prior Publication Data
US 2016/0120416 A1    May 5, 2016

(30) Foreign Application Priority Data
Nov. 4, 2014  (KR) .......................... 10-2014-0152009

(51) Int. Cl.
*A61B 5/04*  (2006.01)
*A61B 7/02*  (2006.01)
*A61B 5/0402*  (2006.01)

(52) U.S. Cl.
CPC ............ *A61B 7/023* (2013.01); *A61B 5/0402* (2013.01)

(58) Field of Classification Search
CPC ..... A61B 5/08; A61B 5/02028; A61B 5/0402; A61B 5/7415; A61B 5/7225; A61B 5/742;
(Continued)

(56) References Cited

U.S. PATENT DOCUMENTS 5,143,078 A  *  9/1992  Mather ................. A61B 7/003
                                                    600/484
6,238,349 B1 *  5/2001  Hickey ................ A61B 5/0215
                                                    600/486
(Continued)

FOREIGN PATENT DOCUMENTS

CN      101518439 B      1/2011
JP        5230161 B2     3/2013
KR     20060088770 A     8/2006

OTHER PUBLICATIONS

Kim, "Prediction of Fluid Responsiveness by a Non-invasive Beat-to-beat Assessment of Ventricular Systolic Time using Heart Sound Signal during Liver Transplantation," A Dissertation, The Graduate School of the University of Ulsan, Department of Medicine, Ulsan, Korea (Translation) (45 pages) (Aug. 2014).

*Primary Examiner* — Mallika D Fairchild
(74) *Attorney, Agent, or Firm* — Seed Intellectual Property Law Group LLP

(57) ABSTRACT

The present invention relates to A system for monitoring the cardiovascular system using a heart sound, which comprises a heart sound receiving means(100) for receiving a heart sound(HS); DSP (Digital Signal Processor) module(200) for converting the heart sound(HS) received from said heart-sound receiving means(100) to a digital signal; and an arithmetic section(300) for calculating phonocardiogram (PCG) from the digital signal converted in the DSP module (200) and calculating information related to a preload or information related to a cardiac contractile force or information related to a respiratory change.

12 Claims, 15 Drawing Sheets

(58) Field of Classification Search
CPC ..... A61B 5/7253; A61B 5/7278; A61B 7/006; A61B 7/023
See application file for complete search history.

(56) References Cited

U.S. PATENT DOCUMENTS

| | | | |
|---|---|---|---|
| 7,174,203 B2 | 2/2007 | Arand et al. | |
| 2005/0222515 A1* | 10/2005 | Polyshchuk | A61B 7/04 600/528 |
| 2006/0106322 A1* | 5/2006 | Arand | A61B 5/0402 600/514 |
| 2006/0173373 A1 | 8/2006 | Shin et al. | |
| 2011/0257548 A1* | 10/2011 | Dong | A61B 7/04 600/528 |
| 2012/0041317 A1* | 2/2012 | Patangay | A61B 5/02028 600/483 |
| 2012/0296228 A1* | 11/2012 | Zhang | A61B 5/0006 600/513 |

\* cited by examiner

SYSTEMS FOR MONITORING THE CARDIOVASCULAR SYSTEM USING A HEART LUNG SOUND

CROSS-REFERENCE TO RELATED APPLICATION(S)

This application claims the benefit of Korean Patent Application No. KR2014-0152009A, filed Nov. 4, 2014, which is hereby incorporated by reference herein in its entirety.

BACKGROUND

1. Technical Field

The present invention relates to systems and methods capable of acquiring necessary data for the monitoring and diagnosis of the cardiovascular system using a heart lung sound.

2. Description of the Related Art

In diagnosing anesthetized patients or seriously affected patients, there is a need to monitor a number of data. By using general monitoring devices currently available, the patient's electrocardiogram, blood pressure, end-tidal carbon dioxide partial pressure, peripheral oxygen saturation and body temperature can be generally monitored.

Although it is not generally monitored, a body fluid content (total blood volume) (below, called "preload" having the same or similar meaning) and a cardiac contractile force can be included as clinically important data.

First, the preload will be described.

For trauma patients or patients undergoing surgery, a rapid change in the blood volume within a short period of time can occur due to bleeding out and the like. At this time, the preload must be known in order to identify the presence or absence of such a change. In other words, when the preload is accurately identified in real time, an appropriate measure such as blood transfusion or fluid infusion can then be taken. Therefore, the preload can be said to be data directly related to the patient's health. Currently, basic monitoring data such as blood pressure or oxygen saturation is acquired using conventional monitoring devices, through which the preload can be indirectly estimated. However, for example, since the blood pressure may be normal until a considerable amount of blood loss occurs, the accuracy is insufficient, thus making effective real-time monitoring difficult.

As another method for evaluating the preload, "response to fluid administration" can be used. This has been designed based on the fact that, if the blood volume of the patient is insufficient upon fluid administration, there is a response which causes an increase in the blood pressure. If the blood pressure increases after the fluid administration, there is a response (response(+)) and thus the preload will be lowered. If there is no response (response(−)), the preload will be sufficient. The response to fluid administration is a method well-known for evaluating whether the blood volume of the patient is appropriate. This is a concept designed to predict the blood volume prior to administration because the fluid administration itself may cause a harmful situation for the patient.

Indices for completely predicting the response to fluid administration have not been known to date. However, a number of monitoring devices that have recently come into the market have been developed in the direction of self-developing the indices representing a response to fluid administration and displaying them on the screen.

Next, the cardiac contractile force will be described.

The blood pressure may be lowered even though the preload is sufficient. This is because the cardiac contractile force is insufficient. As a device for evaluating the cardiac contractile force, only the echocardiography device is currently available. However, since the echocardiography device requires a high skill level for operation and has difficulties in continual monitoring, it is hard to conveniently use this device in actual clinical practice.

Among the data monitoring devices for monitoring. anesthetized patients or seriously affected patients, examples of typical monitoring devices available in the market today are as follows.

Vigilence® device (Edward Lifescience® company) measures various hemodynamic indices with a blood dilution method, and particularly observes whether the cardiac output (CO) increases by more than 10% to 15% due to the fluid administration, thus assessing the condition of the patient. In the case of using the indices of the aforementioned responsiveness of fluid administration, a time delay can occur because of body heat dilution time. Therefore, when a sudden hemodynamic change occurs, the accuracy is low; particularly, since a long conduit of the catheter penetrates into the heart and mounts on a pulmonary artery, health risks may be high.

In the case of Vigileo® device, e.g., another device of Edward Lifescience® company, a stroke volume variation (SVV) is calculated by acquiring the data in the arterial pressure waveform measured in the radial artery and the like. There is a disadvantage in that there is an invasive mounting on ductus arteriosus. There are reports that there is a large degree of error in situations where the administration of a large amount of vasopressor drugs such as sepsis is required.

In the case of NICOM® device (Chita Medical® company), the total blood volume is estimated based on a change of impedance in the thorax measured by attaching the electrical electrodes to the four corners of the thorax. The present device has a fatal defect in that the accuracy is insufficient and the interference signal is applied by the use of an electrocautery during operation.

In addition, devices for heart ultrasound measurements are manufactured by Philips®, GE®, CardioQ®, zonare® and the like, but they have difficulties in continual monitoring, require a high skill level for operation and have a limitation in providing data necessary for anesthetized patients or seriously affected patients.

In short, the conventional devices have disadvantages in that they use invasive methods to increase accuracy and in that some devices not using the invasive methods have low accuracy, require a high skill level for operation and have difficulties in continual monitoring.

Therefore, there is a need to develop devices for providing the preload and the cardiac contractile force when applied to patients undergoing surgery or severe trauma patients. In particular, there is a need to develop devices capable of high accuracy while using a non-invasive method, having an excellent continual monitoring capacity and providing the data irrespective of the skill level of an operator.

A review of the publications related to the present invention will be described as follows.

U.S. Pat. No. 7,174,203 discloses a system for identifying the condition of the heart by continuously conducting measurements of the electrocardiogram data and heart sound parameters and analyzing the hemodynamic condition. This system has advantages in that it uses a non-invasive method, but the preload and the cardiac contractile force are not provided and thus, it fails to acquire the data essentially required for the procedures of the clinical diagnosis and treatment.

Non-patent document, the 2010 paper, "New Temporal Features for Cardiac Disorder Classification by Heart Sound" discloses an algorithm capable of identifying various kinds of cardiac diseases by analyzing the heart sound data. However, this simply identifies direct diseases of the heart, particularly lesions of heart valves, and it fails to provide the data for monitoring anesthetized patients or seriously affected patients other than patients with basal heart diseases.

Japanese Patent No. 5,230,161 discloses a technique of diagnosing cardiac diseases by synchronizing the heart sound data and the electrocardiogram data. Likewise, this fails to provide the data for monitoring anesthetized patients or seriously affected patients other than patients with basal heart diseases.

PRIOR ART DOCUMENTS

U.S. Pat. No. 7,174,203
Japanese Patent No. 5,230,161
Gwak-Cheol, Gwon-Ohuk, "New Temporal Features for Cardiac Disorder Classification by Heart Sound", Journal of the Acoustical Society of Korea, Vol.29. No. 2, pp.133~140, 2010.

SUMMARY

The present invention solves the above-mentioned problems.

More specifically, an objective of the present invention is to acquire hemodynamic data by a non-invasive method, particularly to acquire the data related to a preload and a cardiac contractile force.

Another objective of the present invention is to provide a system capable of increasing the accuracy and the continual monitoring capacity and at the same time allowing a real time monitoring.

Technical Solution

In order to accomplish the above-mentioned objectives, one embodiment of the present invention provides a system for monitoring the cardiovascular system using a heart sound, which comprises a heart sound receiving means(100) for receiving a heart sound(HS); DSP (Digital Signal Processor) module(200) for converting the heart sound(HS) received from said heart-sound receiving means(100) to a digital signal; and an arithmetic section(300) for calculating a phonocardiogram(PCG) from the digital signal converted in the DSP module (200) and calculating information related to a preload or information related to a cardiac contractile force or information related to a change in the respiratory system.

Also, the arithmetic section(300) preferably calculates as a trend at least one of the information related to the preload, the information related to the cardiac contractile force and the information related to a change in the respiratory system.

Moreover, the arithmetic section(300) calculates a time and amplitude of a first heart sound(S1) and a time and amplitude of a second heart sound(S2) in the above calculated phonocardiogram(PCG), and the arithmetic section (300) preferably calculates a systolic time interval(STI) using the difference between the time of the first heart sound(S1) and the time of the second heart sound(S2).

Further, the arithmetic section(300) calculates the systolic time variation(STV) in accordance with a predetermined method utilizing the above calculated systolic time interval (STI), and the information related to the preload is preferably the calculated phonocardiogram(PCG) and the systolic time variation (STV).

Further, the arithmetic section (300) calculates an electromechanical activation time (EMAT) using the above calculated phonocardiogram (PCG) and electrocardiogram (ECG), and the information related to the cardiac contractile force preferably the said electromechanical activation time (EMAT), the amplitude of the first heart sound(S1) and the amplitude of the second heart sound(S2).

Further, the arithmetic section (300) calculates preferably an amplitude conversion ratio using the amplitude of the first heart sound (S1) and the amplitude of the second heart sound(S2).

Further, the arithmetic section (300) calculates preferably the four different treatment information for each case based on whether the systolic time interval (STI) exceeds a predetermined value (A) or whether the amplitude conversion ratio exceeds a predetermined other value (B)

Further, the four different treatment information refers to a first, second, third and fourth treatment information. Preferably, the above arithmetic section (300) calculates the first treatment information when the systolic time interval (STI) exceeds a predetermined value (A) and the amplitude conversion ratio does not exceed a predetermined other value (B); calculates the second treatment information when the systolic time interval (STI) exceeds a predetermined value (A) and the amplitude conversion ratio exceeds a predetermined other value(B); calculates the third treatment information when the systolic time interval(STI) does not exceed a predetermined value(A) and the amplitude conversion ratio exceeds a predetermined other value(B); and calculates the fourth treatment information when the systolic time interval(STI) does not exceed a predetermined value(A) and the amplitude conversion ratio does not exceed a predetermined other value(B).

When diagnosing hemodynamically unstable patients on the basis of such information and determining the direction of a treatment, the four treatment informations are directly useful for choosing a cardiotonic agent administration, a vasoconstrictor administration, a fluid administration or a combined administration thereof.

Further, preferably, the above predetermined value (A) is 300 to 310 ms, and the above predetermined other value(B) is 15%.

Further, the heart sound receiving means (100) is preferably a microphone mounted in the esophagus stethoscope (P).

Further, the DSP module (200) comprises preferably a preamplifier(210) for amplifying the heart sound (HS) received from the heart sound receiving means (100); and filtering means for filtering the heart sounds amplified by the preamplifier (210).

Further, the filtering means (220) comprises preferably ADC (221) for converting the amplified heart sounds into a digital signal; and a BPF (222) for performing band-pass filtering of the converted digital signal.

Further, the BPF (222) performs preferably a band-pass filtering using a frequency band of 8~1000 Hz.

Further, the arithmetic section (300) calculates preferably the phonocardiogram(PCG) by performing a Hilbert transform of the digital signal.

Further, the system for monitoring the cardiovascular system using a heart sound further includes preferably an output section(400) for outputting information related to a preload or information related to a cardiac contractile force calculated from the above arithmetic section (300).

Further, the output section(400) further includes preferably a display unit (410) capable of displaying information related to a preload or information related to a cardiac contractile force calculated from the above arithmetic section (300); and a speaker (420) capable of sound-outputtng the heart sound (HS) received from the heart sound receiving means(100).

In addition, the phonocardiogram(PCG) that is calculated by the DSP module (200) shows its change of time as the X-axis. It is desirable to identify whether the frequency of the phonocardiogram (PCG) deviates from the range of 320-340 Hz upon expiration or whether the frequency deviates from the range of 210-230 Hz upon expiration.

Advantageous Effects

According to the present invention, data which could not be acquired by the prior art or which estimated a preload and a cardiac contractile force with a low accuracy, and data about a change in the respiratory system, can now be acquired with a very high accuracy.

In particular, when using a heart sound (HS), the system of the present invention is configured so as not to be affected by the lung sound, thus increasing the accuracy, and a separate invasive method is not required due to application to an existing tracheal intubation patient.

Regarding accuracy, as will be described in the verification experiments below, the AUC value for the ROC curve analysis has been demonstrated as 0.900. This proves that the accuracy is strongly increased as compared with the AUC value of the conventional CVP which is 0.706.

Moreover, any other type of data can he associated together and displayed on the monitor. In other words, information related to the preload and the cardiac contractile force which can be seen through the present invention can be displayed together with information that can acquire from a conventional general device. Therefore, it is possible to convey the accurate and effective information to the operating surgeon in real time.

Further, various treatment information can be accurately provided in real time by utilizing the value of the systolic time interval(STI) and the amplitude conversion ratio thereof.

In addition, as will be described in the validation experiment(4) below, it is possible to monitor in advance a minimal change in the respiratory system which could not be monitored by the electrocardiogram, end-tidal carbon dioxide partial pressure and airway pressure. Therefore, the present invention is a great help in preventing the occurrence of respiratory complications.

DETAILED DESCRIPTION

Figure 1:
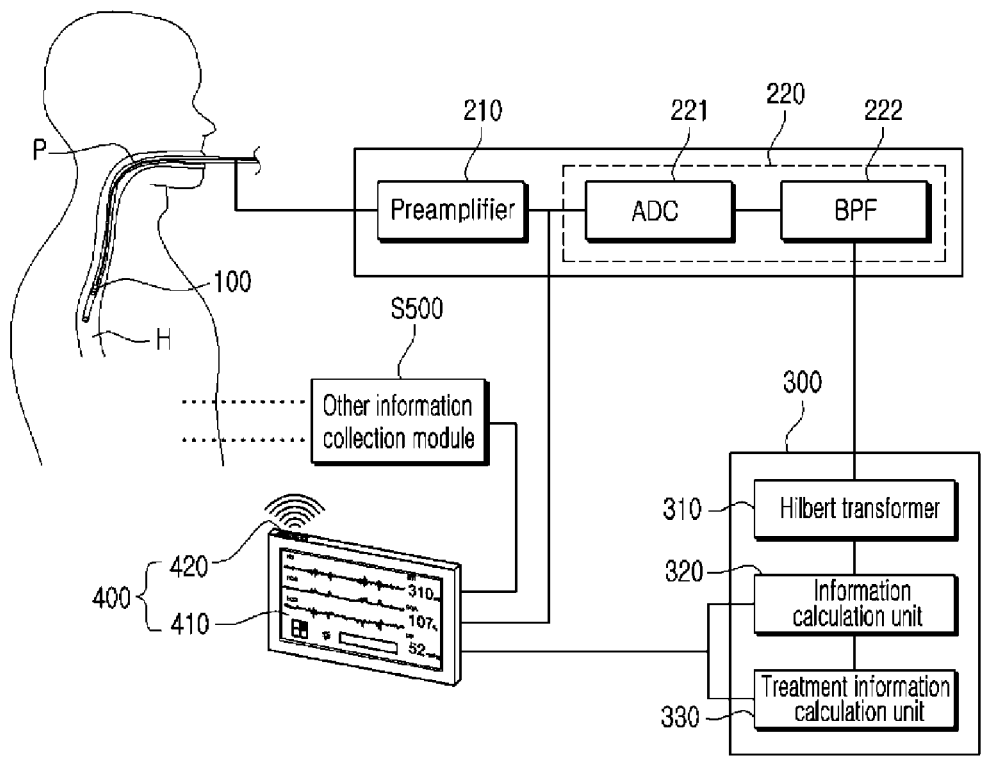
FIG. 1 is a schematic diagram of a system for monitoring the cardiovascular system using a heart sound according to the present invention.

1. Explanation of Terms
ECG: Electrocardiogram
SVV: Stroke Volume Variation
HS: Heart Sound or Heart Lung Sound
PCG: Phonocardiogram
PP: Pulse Pressure(mmHg)
STI: Systolic Time Interval, S1-S2 Interval (ms)
STV: Systolic Time Variation (no unit)
S1 , S2 : First heart sound, second heart sound
ROC curve: Receiver-Operating Characteristic Curve; In order to verify the efficiency of particular diagnostic methods, a plot of a hit probability, i.e., sensitivity as the Y-axis versus its false alarm probability, i.e., 1-specificity as the X-axis.
AUC value: Area Under Curve value (no unit)
EMAT: Electromechanical Activation Time (ms)
LVST: Left ventricular systolic time (ms)
Trend: The degree of variation in the particular value is displayed on the basis of the time and value. For example, a graph showing an electrocardiogram (ECG) and the like.
DSP: Digital Signal Processor
ADC: Analog to Digital Converter.
BDF: Band Pass Filter 2. Description of the Concept of the Present Invention The present invention is based on the fact that the phonocardiogram (PCG) is not, a direct index representing the preload, but when this is processed in an appropriate manner, it can be used as a measure for representing the preload.

Heart sound (HS) is produced by the movement of the valve and the dynamic motion of the blood flow according to the contraction and relaxation of the atrium and ventricles. Therefore, we have acquired the heart sound using a traditional stethoscope and then attempted to use it as information useful for medical practice, but there is a drawback in that it is subjective for every operating surgeon and the accuracy is low.

In an attempt to overcome these drawbacks, the present invention utilizes the phonocardiogram (PCG) acquired through the heart sound (HS). The phonocardiogram (PCG) displays the heart sound (HS) in a visual form and shows a graph including the frequency and amplitude. However, the problems are how to remove a noise which can be inevitably included in the heart sound (HS) and how to extract useful information from the digital signal in which the noise is removed.

There is no objection to the point that the phonocardiogram (PCG) accurately reflects the function and hemodynamic status of the heart. In particular, the present invention relates to an important concept in that, among them, the systolic time interval (STI) is an index related to the preload of the patient. This is due to the principle of "the higher the blood volume in the ventricle, the more time is spent to remove it".

By analyzing the phonocardiogram (PCG), the first heart sound (S1) and the second sound (S2) can be confirmed. The time difference between the first heart sound (S1) and the second heart sound (S2) (S1 and S2 Interval) is the systolic time interval (STI), and there are two reasons why the systolic time interval (STI) is an index related to the preload.

Firstly, the first heart sound (S1 ) is able to listen in relation to the closure of the atrioventricular valve and contain the following four components. When the first contraction of the ventricle movement blood volume toward the atrium is made, the first vibration occurs and the atrioventricular valve is closed. The second component is made by a sudden tension of the closed atrioventricular valve. The third component indicates the vibration of blood flow between the aortic root and the ventricular wall. The fourth component is associated with the vibration due to the flow of blood in the inside of the large blood vessels.

Secondly, the second heart sound (S2) indicates the end of cardiac contractions and the beginning of the heart relaxation and it is able to listen at the closing time of the aortic and the pulmonary valve. The second heart sound (S2) is the result of vibration of the cardiovascular system by decelerating and reversing the flow of blood to the inside of the pulmonary artery and the aortic.

Accordingly, the systolic time interval (STI) which is the time difference between the first heart sound (S1) and the second heart sound (S2) can be an index related to the preload. In this regard, through the opening and closing time interval of the both valves, it can be conceived that the blood must be discharged to the left ventricular outlet of the same area and thus, the greater the amount of blood that remains in the heart during the core cycle, the more time is required. In particular, it has been confirmed from the validation experiment (1) below that the systolic time interval (STI) is very closely related to the pulse pressure (PP). Thus, it can be said to demonstrate this.

In the following, as described above, the particular system of the present invention for acquiring the phonocardiogram (PCG) with a high accuracy, and the specific calculation method of the present invention for extracting clinically useful information from the acquired phonocardiogram (PCG) are described sequentially.

3. Description of System

Referring to FIG. 1, the system for monitoring the cardiovascular system using a heart sound according to the present invention will be described.

The system for monitoring the cardiovascular system using a heart sound according to the present invention includes a heart sound receiving means (100), a DSP module (200), an arithmetic section (300) and an output section (400).

The heart sound receiving means (100) may be a microphone. The heart sound receiving means (100) can be inserted in the body of patient (H) using another device, but it is preferable to use the catheter type of esophageal stethoscope (P) which is previously inserted and mounted into the esophagus of a patient (H). In other words, it is preferable to mount a small microphone as a heart sound receiving means (100) in esophagus stethoscope (P). Further, it is possible to use the type in which a small microphone is attached to the other sites in the outside end or the middle point of the heart sound stethoscope.

The heart sound receiving means (100) receives the heart sound (HS) and transmits it to the DSP module (200).

The DSP module (200) includes a preamplifier (210) and a filtering means (220).

The preamplifier (210) may be any type of amplifier for amplifying the received heart sound (HS).

The filtering means (220) digitize the amplified heart sound and at the same time filter it.

Specifically, the filtering means (220) include ADC (221) and BPF (222).

ADC (200) converts the amplified heart sound, namely an analog signal to a digital signal.

BPF (222) performs a band pass filtering of the digital signal of the converted heart sound. At this time, it is preferable to use a frequency band with a low frequency at 8 to 1000 Hz. This is because most of the noise which may be collected by esophageal stethoscope (P) has a high frequency.

Preferred forms of DSP modules (200) are described in the above, but specific circuits and the like are well-known conventional techniques and so detailed description thereof is omitted.

The arithmetic section (300) calculates a variety of information based on the digital signal of the heart sound (HS) converted by the DSP module (200). The arithmetic section (300) may be any terminal, such as a computer or a server which have an information processing function. Using a computer is preferred because the DSP module (200) can be associated with the arithmetic section (300) using a USB standard, and also other data from an electrocardiogram (ECG) can be stored and processed together.

The arithmetic section (300) includes a Hilbert transformer (310), an information calculation unit (320) and a treatment information calculation unit (330).

Figure 2:
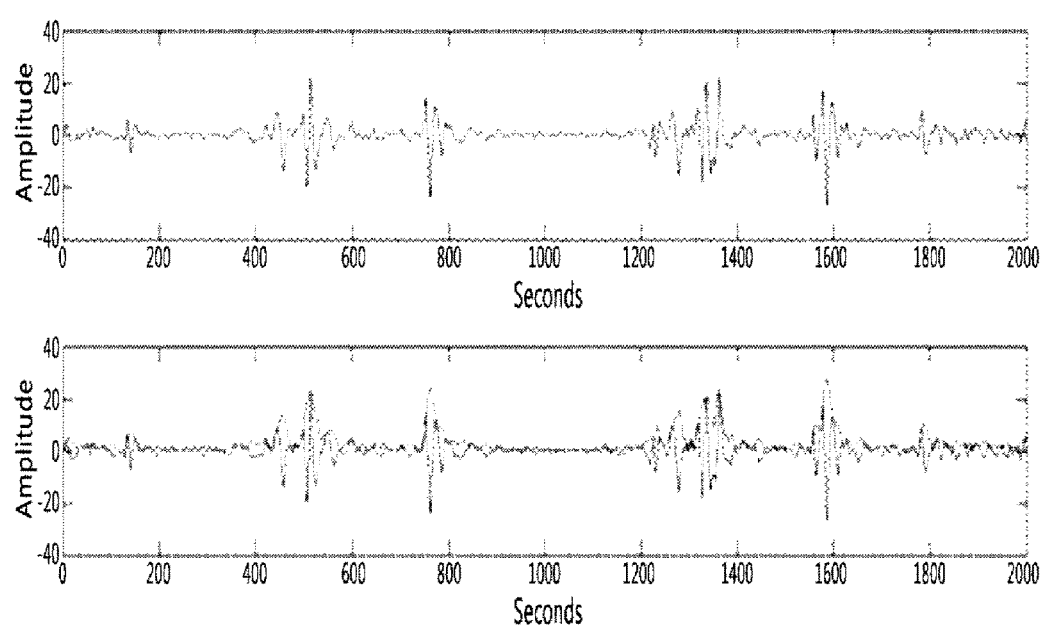
FIG. 2 is a graph explaining a method for calculating the phonocardiogram(PCG) by a Hilbert transform.

The Hilbert transformer (310) performs a Hilbert transform of a digital signal transmitted from the DSP module (200) to calculate the phonocardiogram (PCG). The Hilbert transform itself is a conventional technique and so detailed description thereof is omitted. The upper graph in FIG. 2 shows a digital signal before the Hilbert transform in blue, and the lower graph in FIG. 2 shows a digital signal after the Hilbert transform in red. As shown in FIG. 2, when the Hilbert transform is performed, the phonocardiogram (PCG) is calculated and so the time and amplitude of the first heart sound (S1), and the time and amplitude of the second heart sound (S2) can be easily confirmed. Further, the interval between the first heart sound (S1) and the second heart sound (S2) (S1 -S2 Interval) is calculated in real time as the systolic time interval (STI).

The information calculation unit (320) calculates a clinically useful information using the phonocardiogram (PCG). The specific calculation method is described below.

The treatment information calculation unit (330) calculates the information calculated by the information calculation unit (320); specifically, it calculates the treatment information using the systolic time interval (STI) and the amplitude conversion ratio. The specific calculation method is described below.

The output section (400) outputs the information calculated by the information calculation unit (320) and the treatment information calculated by the treatment information calculation unit (330).

The output section (400) includes a display unit (410) for visually outputting information and a speaker (420) for outputting a sound. The necessary information can be printed using a printer (not shown), and be associated with the electronic medical record server (not shown) and then the corresponding data is transmitted thereto.

Meanwhile, the output section (400) can be associated with another other information collecting module (500) and outputted together with other information in addition to the information calculated by the system according to the present invention. For example, it is associated with the electrocardiogram device and outputted together with the electrocardiogram (ECG).

Figure 3:
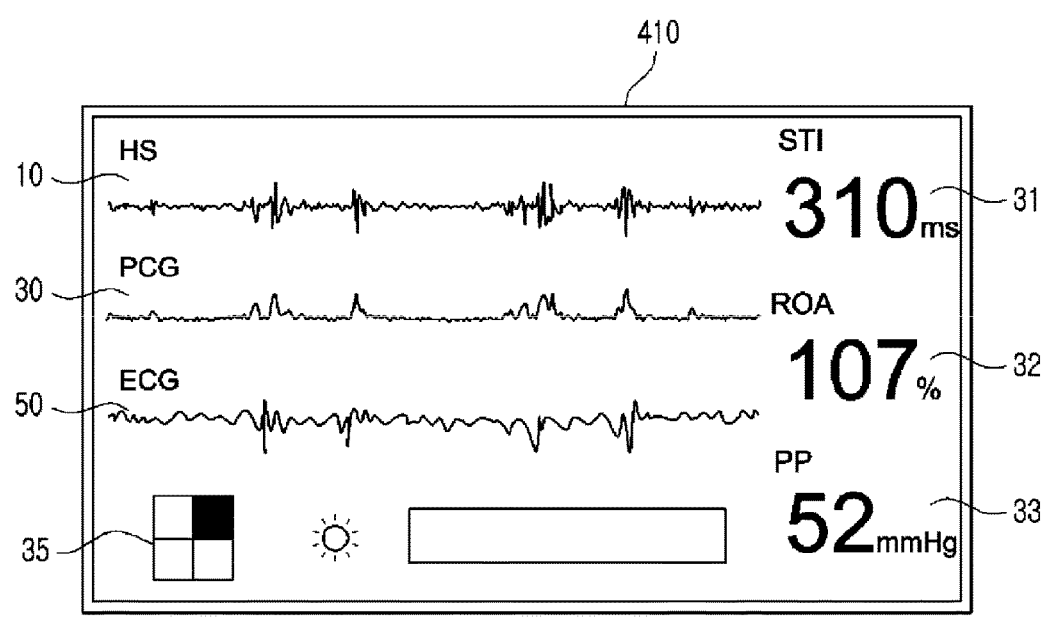
FIG. 3 is a diagram showing an embodiment of an output section of the system for monitoring the cardiovascular system using a heart sound according to the present invention.

FIG. 3 illustrates one embodiment of an output section (400). The trend of the heart sound (HS) is shown in the area "10", the trend of the phonocardiogram (PCG) is shown in the area "30", and the electrocardiogram (ECG) obtained in the electrocardiogram device, one of the other information collection means (500), is shown in a region "50". Further, the value of the systolic time interval (STI) is shown in the area "31", the amplitude conversion ratio (ROA) is shown in the area "32", and the pulse pressure (PP) is shown in the region "33". Moreover, different treatment information calculated by the treatment information calculation unit (320) is classified and shown in the area "34". In particular, regarding the treatment information, as shown, it is preferable to output the information in the form of "2×2,", which is intended to provide the treatment information visually as described below with reference to FIG. 5.

Meanwhile, the speaker (420) outputs heart sound (HS) received from the heart sound receiving means (100) into a voice or outputs the heart sound amplified and modulated by the preamplifier (210) into a voice, and thus the operating surgeon can listen the voice directly, if desired.

4. Description of the Calculation Method

Figure 4:
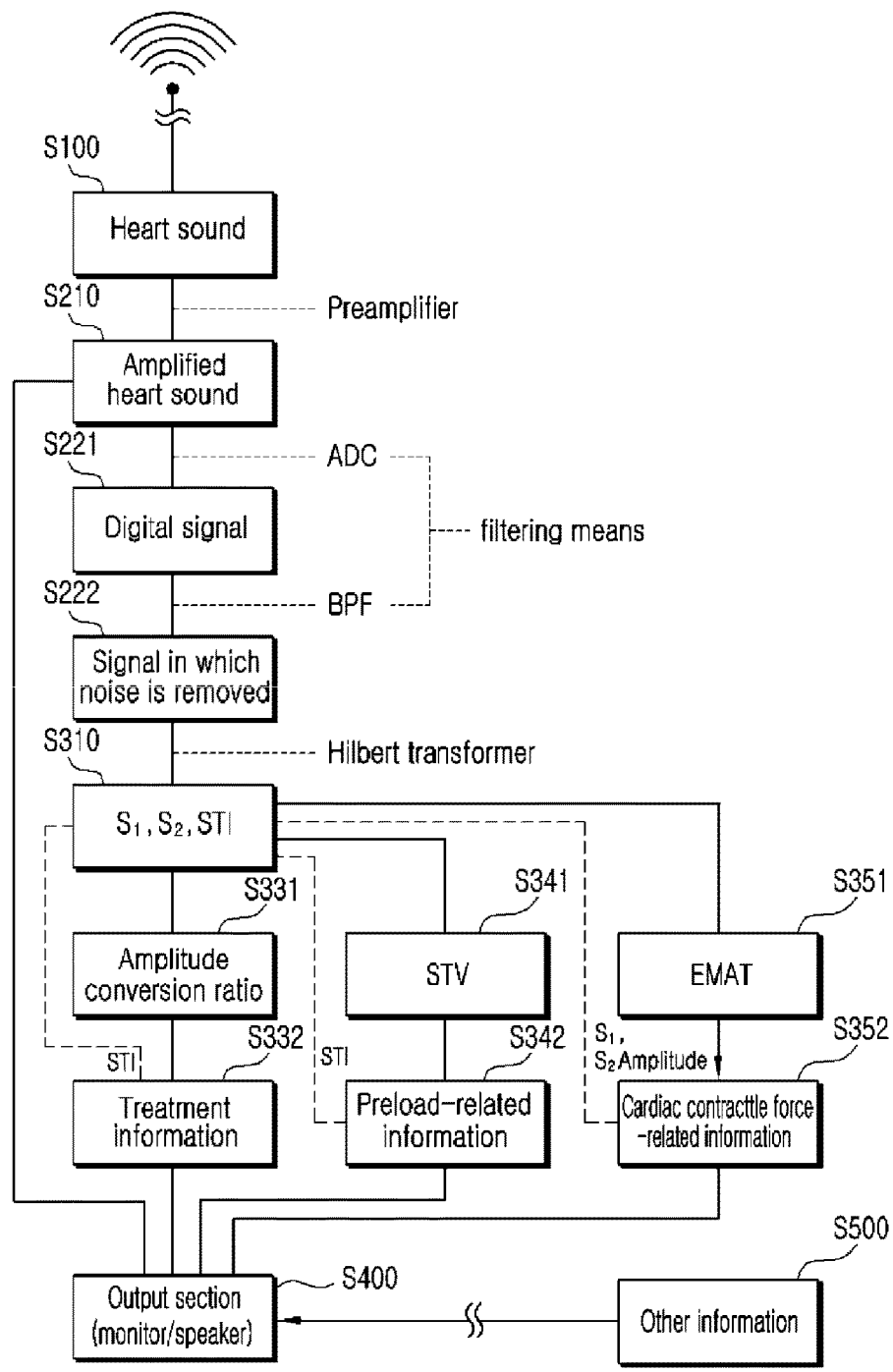
FIG. 4 is a flowchart illustrating a method for calculating the information using the heart sound (HS) in the system for monitoring the cardiovascular system using a heart sound according to the present invention.

Next, the method of calculating information using the system according to the present invention is described with reference to FIG. 4.

STI

For example, the heart sound receiving means (100), a small microphone, receives a heart sound (HS) (S100). The heart sound (HS) received by the heart sound receiving means (100) is transmitted to the preamplifier (210) of the DSP module (200) and then amplified.

The amplified heart sound (HS) (S210) is a digital signal (S221) via ADC (221). The digital signal (S221) performs a band pass filtering in EDF (222). As previously described, it is desirable to perform the filtering using a frequency band with a low frequency at 8~1000 Hz.

The noises such as a lung sound or a fricative sound in digital signals are removed by such filtering. The signal (S222) from which noise has been removed is transmitted to Hilbert transformer (310).

The Hilbert transformer (310) performs Hilbert transform of the signal (S222) from which noises have been removed, thus calculating the phonocardiogram (PCG). As previously described, if the Hilbert transform is performed, the phonocardiogram (PCG) is calculated, and so the time and amplitude of the first heart sound (S1), and the time and amplitude of the second heart sound (S2) are confirmed. Further, the interval between a first heart sound (S1) and a second heart sound (S2) (S1-S2 Interval) is calculated as a systolic time interval (STI) (S310).

As described in detail in the validation experiment (1) below, the present inventors have found that the systolic time interval (STI) is very similar to the pulse pressure (PP) measured in an invasive manner in the lumbar artery and has a close change pattern. Typically, the operating surgeon can determine the hemodynamic status, such as the preload, by analyzing the pulse pressure value or change pattern measured in an invasive manner. Therefore, since the systolic time interval (STI) accurately reflects the pulse pressure, it is possible to calculate a variety of treatment information on the basis of whether the interval exceeds a predetermined value (A).

Amplitude conversion ratio and treatment information

The amplitude conversion ratio (S331) can be confirmed by comparing an amplitude of the first heart sound (S1) with an amplitude of the second heart sound (S2). The amplitude conversion ratio is used together with the systolic time intervals (STI) having a change pattern similar to the pulse pressure (PP) or as the reference for determining respective separate treatment information (S332).

Figure 5:
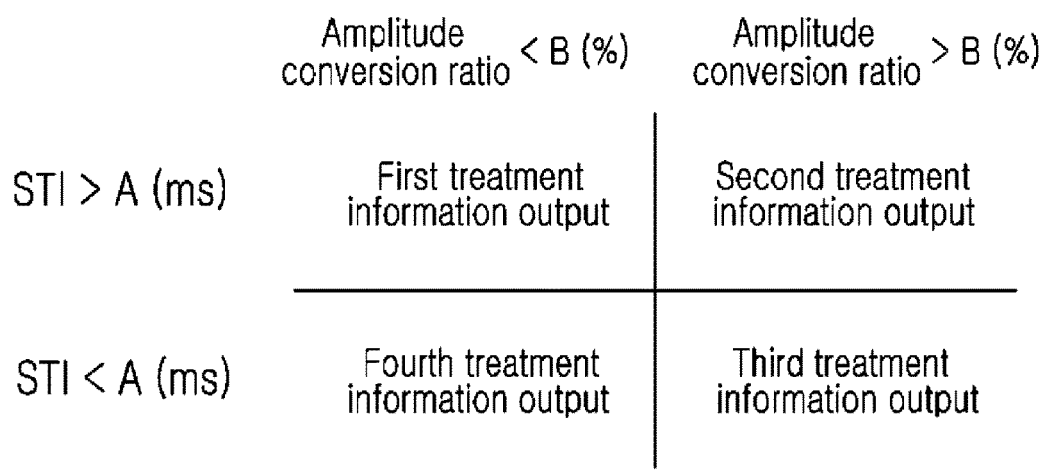
FIG. 5 is a schematic view explaining a method for calculating the treatment information in the system for monitoring the cardiovascular system using a heart sound according to the present invention.

That is, as shown in FIG. 5, whether the systolic time interval (STI) exceeds a predetermined value (A) is set to a first reference, and whether the amplitude conversion ratio exceeds a predetermined other value (B) is set to a second reference. Thus, it is possible to obtain the four different treatment information for each case.

The four treatment informations can be referred to as a first, second, third, and fourth treatment information.

Herein, the first treatment information is a "cardiotonic agent administration"; the second treatment information is a "vasoconstrictor administration"; and the third treatment information may be a "fluid administration". The fourth treatment information is in a state where the systolic time interval (STI) is low and the amplitude conversion ratio is also low and thus, it may be a "combined administration of cardiotonic agent and fluid" which combines the first treatment information with the third treatment information.

If the treatment information is calculated in this way, each of the information is outputted differently via the output section (400). For example, each of the information can be represented in different colors and outputted in a button form, or it can output the reference number itself of the systolic time interval (STI) in a different color.

STV

The systolic time variation (STV) can be calculated using the phonocardiogram (PCG). The systolic time variation (STV) is calculated by the difference between the maximum value (STmax) and the minimum value (STmin) of the phonocardiogram value with respect to the average (STmean) of the phonocardiogram value (i.e., the value of the amplitude) for a predetermined cardiac cycle, for example for 5 to 15 cycles. This is explained by the following formula (1).

Meanwhile, the systolic time variation (STV) is information related to the preload together with the systolic time variation. (STV) as previously described.

$$STV = \frac{ST_{max} - ST_{min}}{ST_{mean}} \quad \text{[Formula 1]}$$

Meanwhile, the information related to such preload is graphically calculated as a trend and the user's readability can be increased.

EMAT

Figure 6:
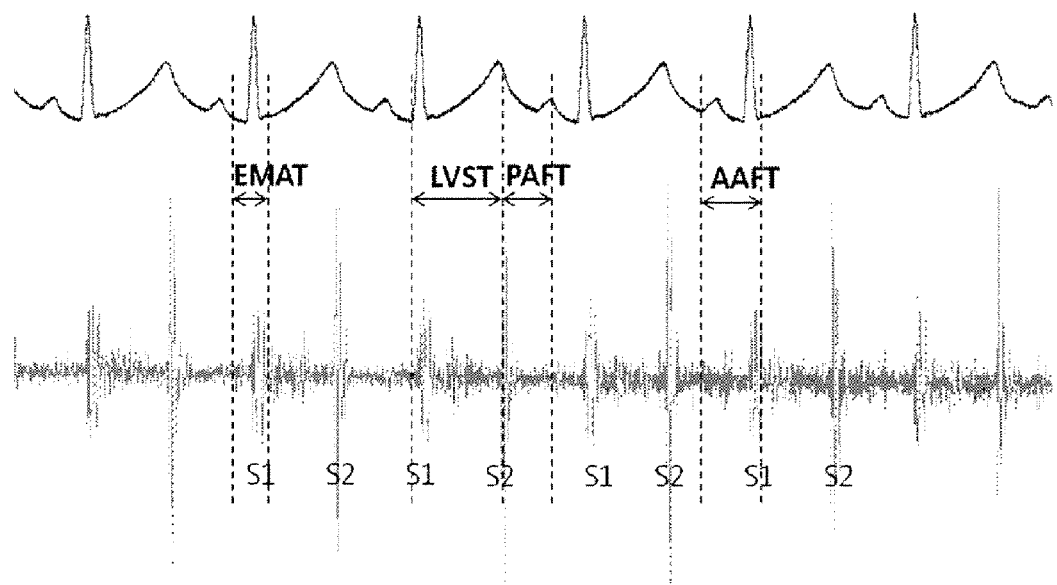
FIG. 6 is a diagram illustrating information that can be obtained by utilizing the system for monitoring the cardiovascular system using a heart sound according to the present invention together with the electrocardiogram (ECG).

As shown in FIG. 6, if the phonocardiogram (PCG) acquired according to the present invention is calculated together with the electrocardiogram (ECG), a variety of information can be calculated. That is, collecting the electrocardiogram (ECG) from the other information collection module (500) allows calculation of various information.

For example, the electromechanical activation time (EMAT) can be acquired based on the interval between the Q wave and the first heart sound (S1) on the graph of an electrocardiogram (ECG).

Thus, the electromechanical activation time (EMAT) is first established as additional information related to the cardiac contractile force together with the amplitude of the first heart sound (S1) and the amplitude of the second heart sound (S2) which have been calculated first.

Meanwhile, the information related to such cardiac contractile force may also be graphically calculated as a trend and so the user's comprehension can be increased.

5. Verification Experiment

Verification Experiment (1)

Based on the data stored on the electronic medical record with a sampling frequency at 1000 Hz during operation, the systolic time interval (STI) was calculated. The pulse pressure (PP) was extracted from the invasive arterial pressure simultaneously recorded in the same record, and compared with the calculated systolic time interval (STI).

Figure 7A:
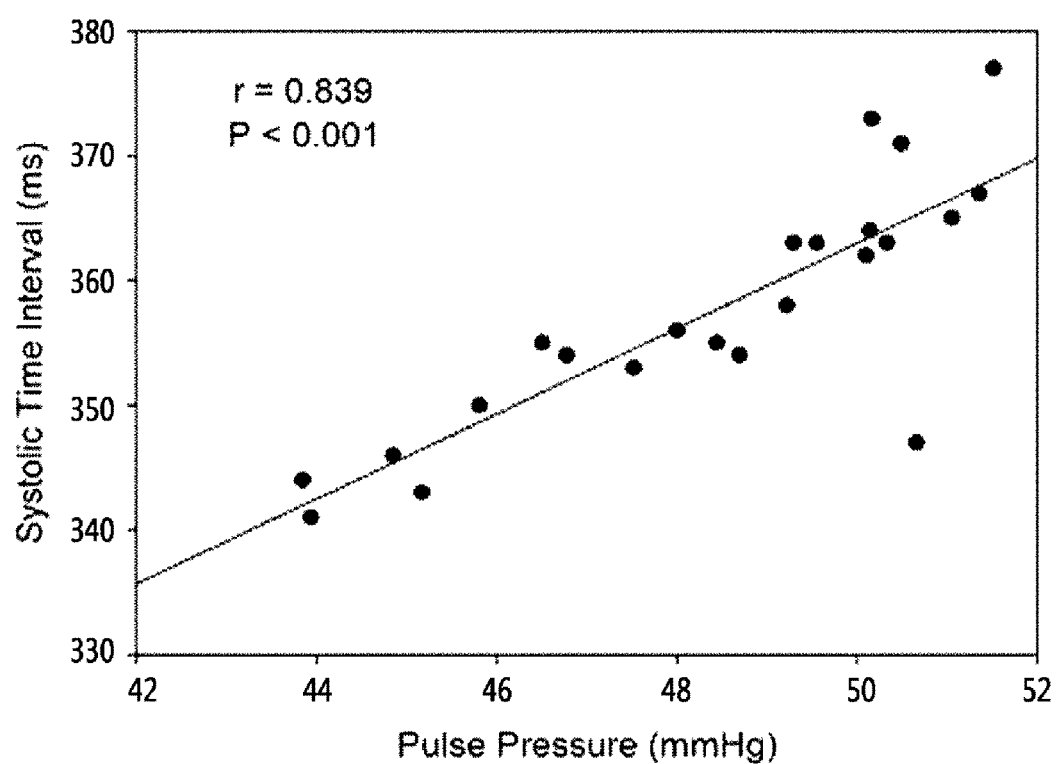
FIGS. 7a and 7b are graphs showing the results of the verification experiment(1) which verifies the correlation between the phonocardiogram (PCG) and the pulse.

FIG. 7a is a graph shown by setting the systolic time interval (STI) as the Y-axis and the pulse pressure (PP) as the X-axis, and confirms that there is a correlation between them and that it shows a similar change pattern in real time.

Figure 7B:
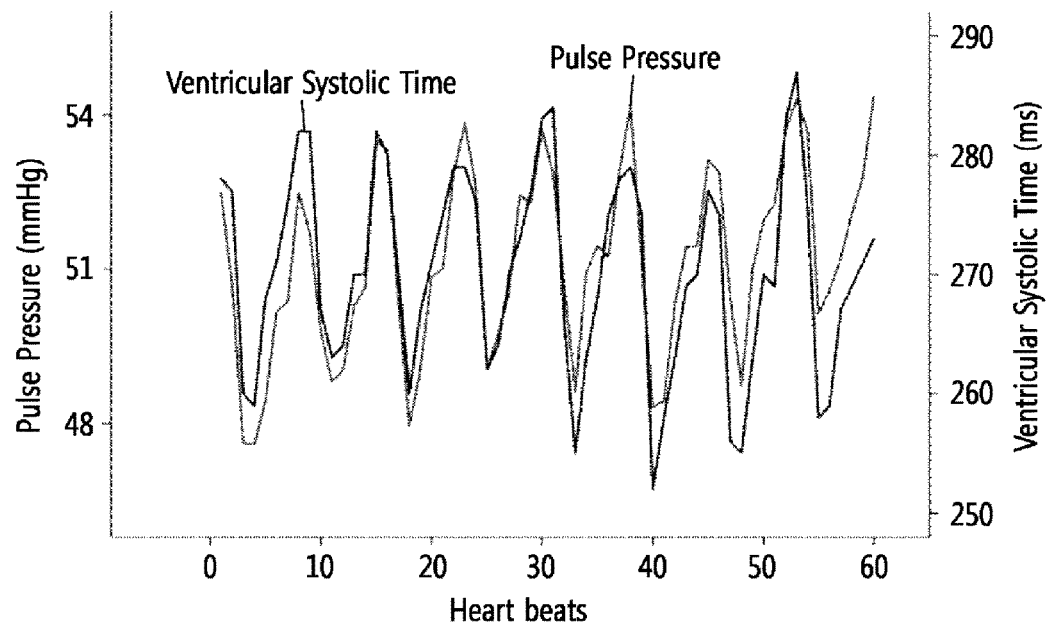

FIG. 7b is a graph shown to confirm the change pattern. The result of the analysis confirmed that the correlation is high at a median value r=0.77 of Pearson correlation coefficient.

Thus, it was confirmed that the systolic time interval (STI) is an effective index showing the pulse pressure (PP). It was also proven that it is effective to provide the treatment information uing the systolic time intervals (STI) as previously described.

Verification Experiment (2)

In the situation where hypovolemia is clinically suspected under operation, when 500 ml of 5% albumin was administrated to 18 patients, the ROC curve analysis was performed in order to predict the response to fluid administration.

Figure 8:
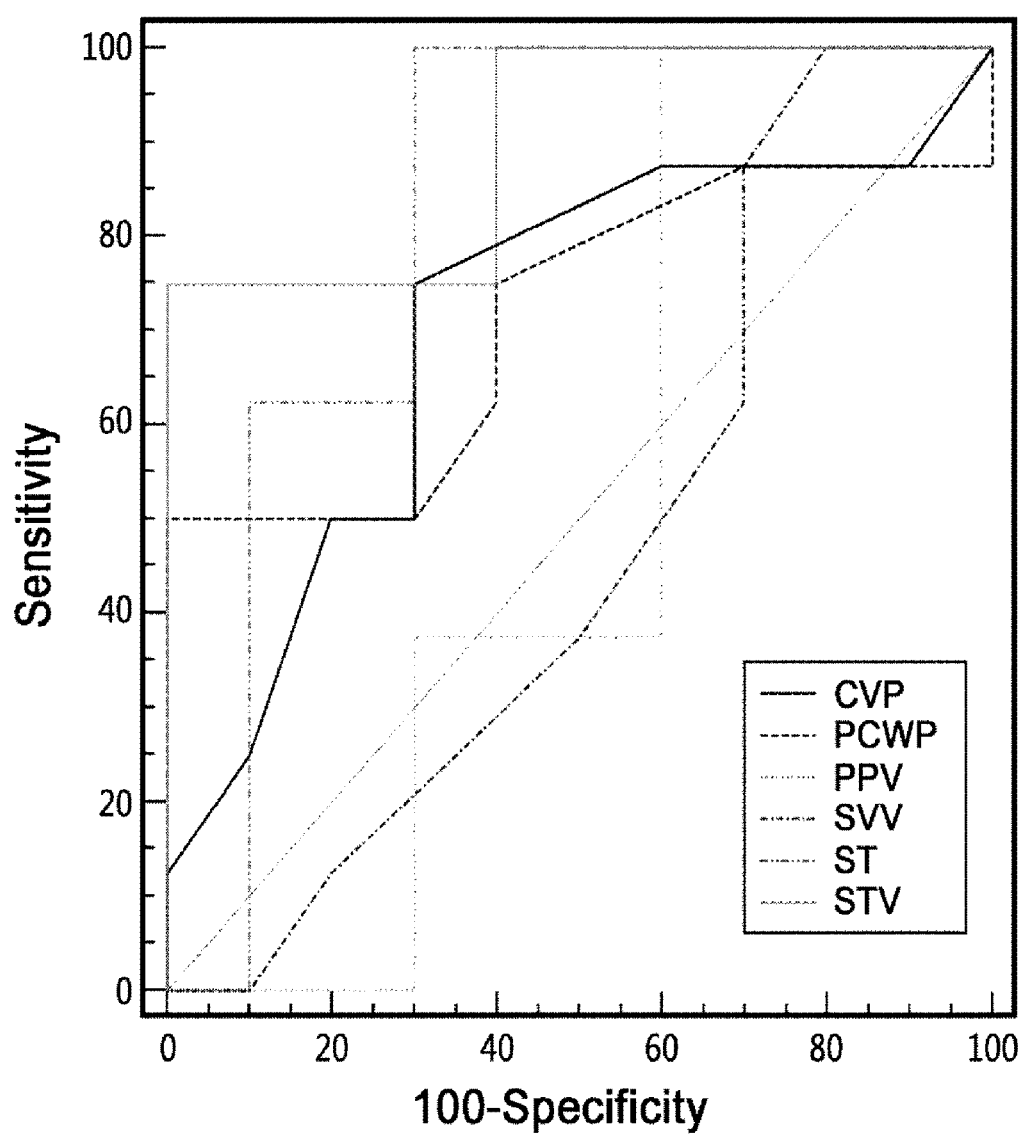
FIG. 8 is a ROC curve showing the result of the verification experiment(2) which verifies the system for monitoring the cardiovascular system using a heart sound according to the present invention.

If the cutoff value was set to STI=308 ms, the AUC value of the systolic time interval (STI) for the response to fluid administration was 0.825 and the AUC value of the systolic time variation (STV) was 0.900 (see Table 1 and FIG. 8).

This was a significantly high value as compared with the static index, i.e., CVP (Central Venous Pressure) or PCWP (Pulmonary Capillary Wedge Pressure), or the dynamic index, i.e., PPV (Pulse Pressure Variation) or SVV (Stroke Volume Variation).

TABLE 1

|      | AUC   | Standard Error | P value* | 95% Confidence Interval |
|------|-------|----------------|----------|-------------------------|
| CVP  | 0.706 | 0.128          | 0.255    | 0.449 to 0.892          |
| PCWP | 0.712 | 0.127          | 0.209    | 0.455 to 0.896          |
| PPV  | 0.512 | 0.141          | 0.729    | 0.271 to 0.750          |
| SVV  | 0.475 | 0.140          | 0.391    | 0.240 to 0.718          |
| STI  | 0.825 | 0.0997         | 0.012    | 0.576 to 0.958          |
| STV  | 0.900 | 0.0815         | 0.007    | 0.667 to 0.986          |

Therefore, it was confirmed that the systolic time intervals (STI) or the systolic time variation (STV) has a high distinction ability for the hypovolumia. In other words, it was confirmed that the preload of the patient could he estimated with a high accuracy.

Further, it was concluded through the above that the cutoff value STI=308 ms is suitable for use as a reference value for the fluid administration. Here, it is preferable to set the cutoff value to 308 ms in order to maintain the proper ALTO values. Through numerous experiments, it was confirmed that it is preferable to set the cutoff value in the range of 300~310 ms. In other words, it was confirmed that the predetermined value (A) of the systolic time interval (STI) as the standard for the treatment information acquirement as described with reference to FIG. 5 was preferably 300 to 310 ms.

Verification Experiment (3)

The information about the cardiac contractile force was basically calculated as compared with the amplitude variation of the heart sound during a particular period of time. The results of the verification experiment thereon are as follows.

Figure 9:
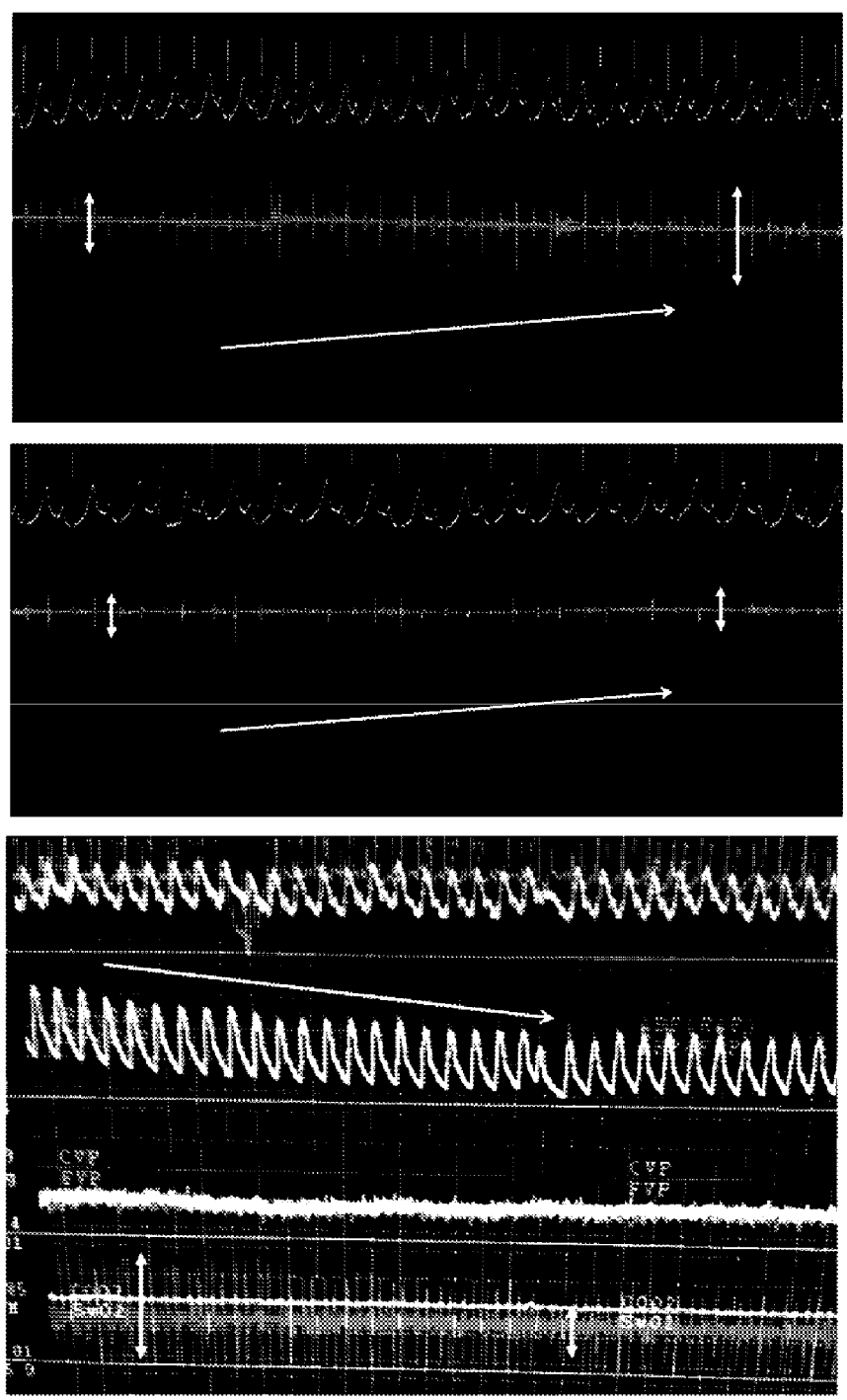
FIG. 9 shows images in which the results of the verification experiment(3) which verifies the system for monitoring the cardiovascular system using a heart sound according to the present invention are taken by those indicated by a display device which is one example of the output section.

As shown in FIG. 9, in case where the blood pressure is elevated due to an increase in the cardiac contractile force, it could be confirmed that the amplitude of the phonocardiogram was increased simultaneously. On the other hand, in the case where the blood pressure is elevated due to an increase in the peripheral vascular resistance, the amplitude of the phonocardiogram is not changed and only the blood pressure is elevated. Further, in the case where the blood pressure is lowered due to a reduction in the cardiac contractile force, it could be confirmed that the amplitude of the phonocardiogram decreases at the same time.

Thus, in order to clinically confirm the information about the cardiac contractile force, the amount of change of the amplitude at the particular point of time as well as during a specified period of time before and after the confirmation must be able to be checked numerically and visually. The amount of change in such cardiac contractile force can be monitored by presenting the absolute value of the heart sound amplitude as well as its relative change amount (%). Therefore, it was confirmed through the present experiment that it is possible to draw information related to the cardiac contractile force using the system for monitoring the cardiovascular system using a heart lung sound in accordance with the present invention.

Verification Experiment (4)

Figure 10A:
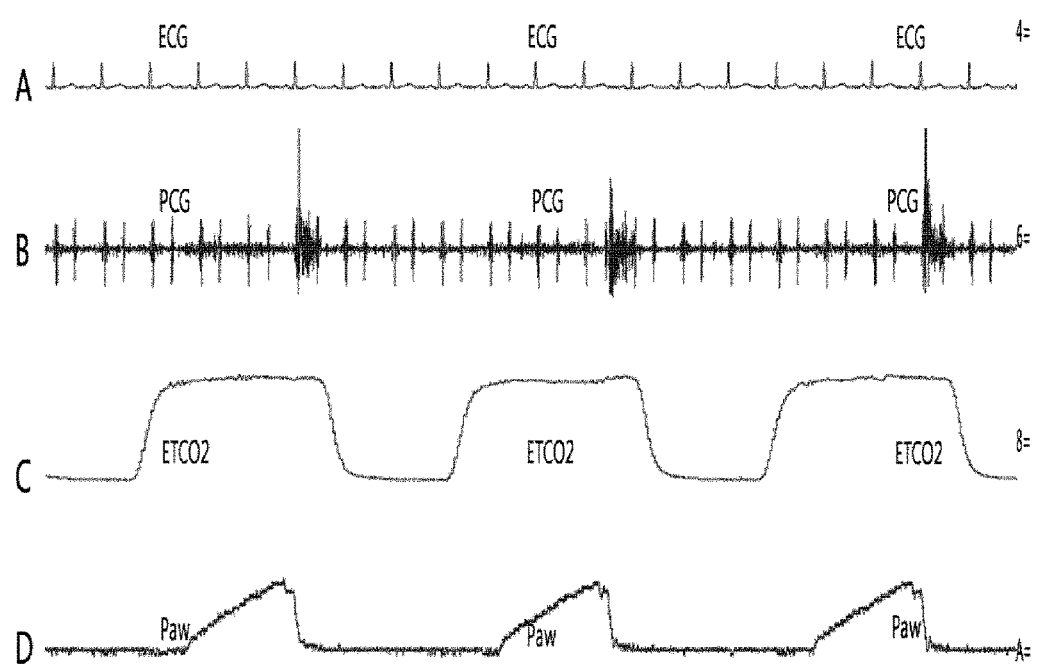
FIGS. 10a through 10c show the results of the verification experiment(4) which verify the system for monitoring the cardiovascular system using a heart sound according to the present invention.
Figure 10B:
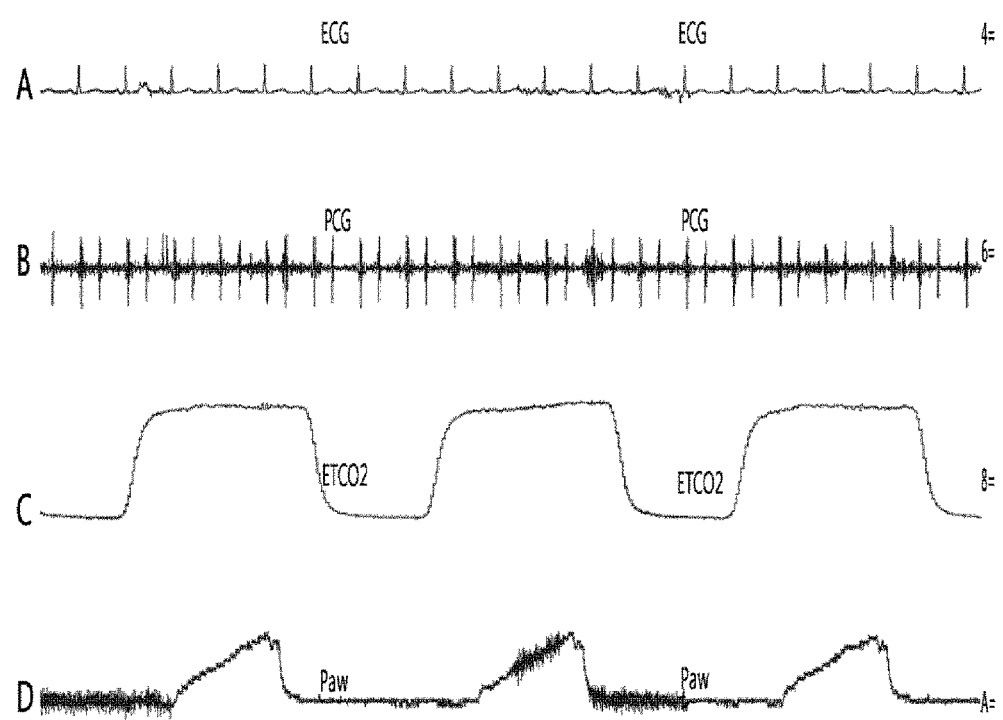

Each of A, B, C and D in FIGS. 10a and 10b are the extended electrocardiogram (ECG), the phonocardiogram (PCG), end-tidal carbon dioxide partial pressure (ETCO2), and the airway pressure (PAW). Herein, the phonocardiogram (PCG), of "B" is a unique result which is confirmed by the system according to the present invention.

In FIG. 10a, the patients are patients with an accumulation of secretions in the trachea. FIG. 10a shows the result of the measurement before the complications occur. The singularity cannot be confirmed from the electrocardiogram and end-tidal carbon dioxide partial pressure. The airway pressure is 20 cm H2O which suggests that there is resistance in the respiratory system. However, those values are not high and so clear identification is difficult.

However, as the measurement results of the phonocardiogram (PCG) according to the invention, the intermittent high frequency noise is identified at the interval of about 6-8 seconds, and so it was possible to suspect singularity.

Thus, it can be seen that it is possible to identify respiratory patients which were difficult to be confirmed by the electrocardiogram, the end-tidal carbon dioxide partial pressure and the airway pressure.

FIG. 10b shows the measurement in the course of suctioning the secretion of the patient in FIG. 10a with a negative pressure device. Herein, the electrocardiogram, end-tidal carbon dioxide partial pressure (ETCO2), and the airway pressure (PAW) do not show particular differences, but it could be confirmed that the phonocardiogram (PCG) according to the present invention can confirm the differences.

Figure 10C:
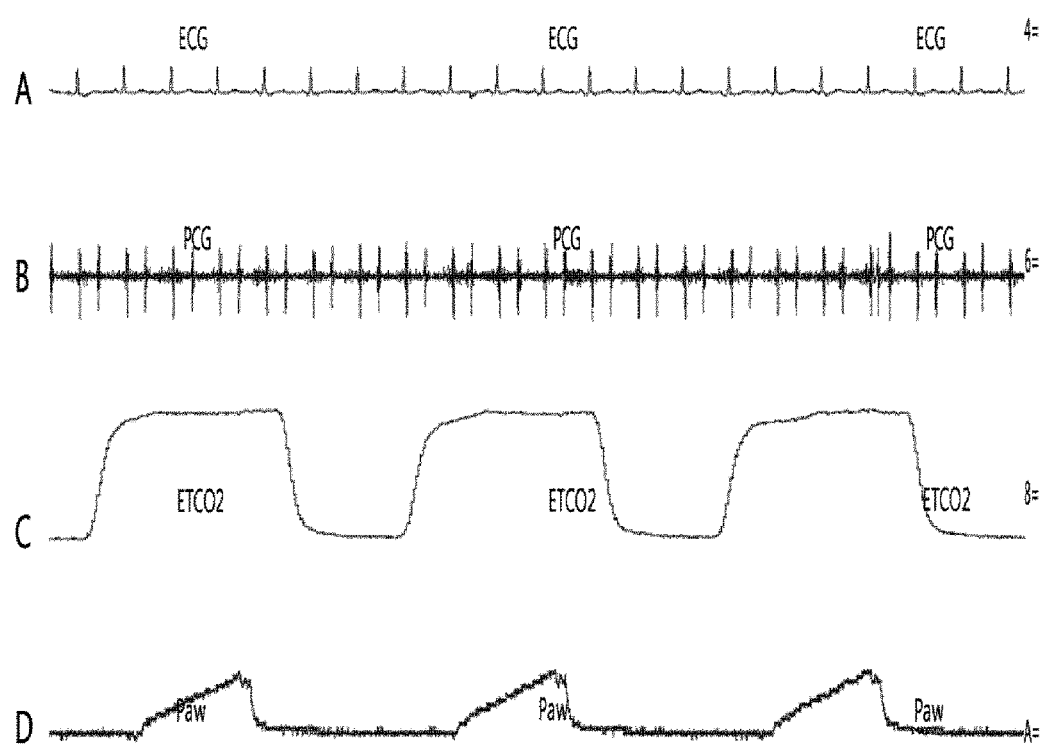

FIG. 10c shows the result of the measurement of the patients in which secretion of the patient in FIG. 10b has been removed. It could be confirmed that the measurement result of the phonocardiogram (PCG) was returned to normal.

Through the above verifications, it was confirmed that it is possible to provide useful information which is difficult to be confirmed by the electrocardiogram, end-tidal carbon dioxide partial pressure (ETCO2), and the airway pressure (PAW).

In particular, it was confirmed that it is possible to screen in advance a minimal change in the respiratory system. That is, it was confirmed through the present experiment that the phonocardiogram (PCG) allows calculation of information related to the preload or information related to the cardiac contractile force or information related to a change of the respiratory system.

This is because the phonocardiogram (PCG) regularly occurs according to the respiratory cycle; a high frequency is generated in response to vibrations being occurring when there is a secretion; and further such high frequency is intermittent only when the direction and speed of air movement are generated in certain cases.

It was confirmed that the frequency of the phonocardiogram (PCG) in a normal breathing state is within the range of 320 to 340 Hz and that the frequency upon expiration is within the range of 210 to 230 Hz. Therefore, based on that the phonocardiogram (PCG) measured using the system according to the present invention deviates from the above range, the specificity will be confirmed, through which early screening of a minimal change in the respiratory system is possible.

Verification Experiment (5)

Figure 11A:
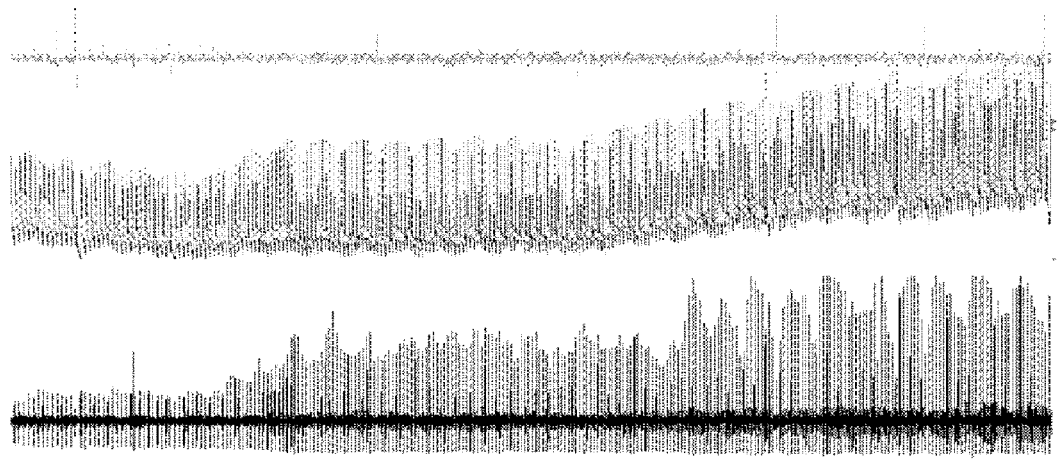
FIGS. 11a and 11b show the results of the verification experiment (5) which verifies the system for monitoring the cardiovascular system using a heart sound according to the present invention.
Figure 11B:
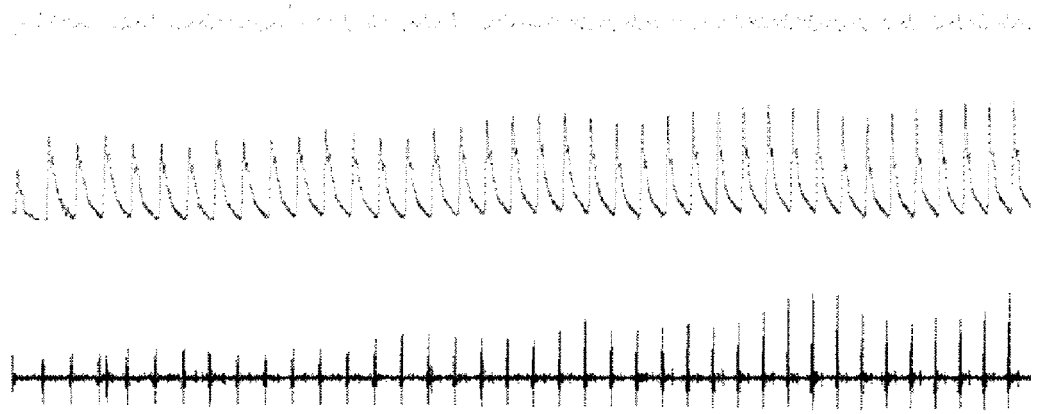

FIGS. 11a and 11b show the electrocardiogram (ECG), the blood pressure (invasive measurement) and the phonocardiogram (PCG) of the patients administrated with a cardiac contractor, respectively, in turn, in accordance with the present invention.

FIG. 11b is an enlarged view of the time scale in FIG. 11a. It can be seen that the magnitude is not only increased gradually, but also the change of the blood pressure measured invasively and the phonocardiogram (PCG) correspond to a ratio of 1:1. In particular, it can be seen that the amplitude of the phonocardiogram (PCG) is sensitively changed even in a minimal change of the blood pressure.

By this verification experiment, it can be seen that a change of the preload and the cardiac contractile force is reflected in real time in the phonocardiogram (PCG).

In the above, the present invention has been described with reference to preferred embodiments, but it will be understood to a person having ordinary skill in the art that various changes and modifications are made to the present invention without departing from the spirit and scope of the present invention described in the claims below.

DESCRIPTION OF REFERENCE NUMERALS

100: heart sound receiving means
200: DSP (Digital Signal Processor) module
210: Preamplifier
220: filtering means
221: ADC (Analog to Digital Converter)
222: BDF (Band Pass Filter)
300: Arithmetic section
310: Hilbert transformer
320: Information calculation unit
330: Treatment information calculation unit
400: Output section
410: Display unit
420: Speaker
500: Other information collection module

What is claimed is:

1. A system for providing treatment information using phonocardiogram, the system comprising:
   a heart sound receiving means for receiving heart sounds;
   DSP (Digital Signal Processor) module for converting the heart sounds received from said heart-sound receiving means to digital signals;
   an arithmetic section for calculating phonocardiogram from the digital signals converted in the DSP module and calculating treatment information for fluid administration; and
   an output section for outputting the calculated phonocardiogram and the calculated treatment information,
   wherein the arithmetic section:
   i) calculates a time and an amplitude of a first heart sound and a time and an amplitude of a second heart sound from the calculated phonocardiogram,
   ii) calculates a systolic time interval using the difference between the time of the first heart sound and the time of the second heart sound and calculates an amplitude conversion ratio using the amplitude of the first heart sound and the amplitude of the second heart sound,
   iii) determines whether the calculated systolic time interval exceeds a predetermined first reference value and whether the calculated amplitude conversion ratio exceeds a predetermined second reference value, and
   iv) calculates the treatment information for fluid administration corresponding to the calculated systolic time interval and the calculated amplitude conversion ratio, based on the determination in the step of iii), the treatment information for fluid administration being one of predetermined four treatment informations.

2. The system for providing treatment information using phonocardiogram according to claim 1, wherein the arithmetic section calculates information related to cardiac contractile force using the calculated phonocardiogram, and wherein the arithmetic section calculates as a trend at least one of the treatment information for fluid administration and the information related to the cardiac contractile force.

3. The system for providing treatment information using phonocardiogram according to claim 1, wherein the arithmetic section calculates the systolic time variation in accordance with a predetermined method utilizing the calculated systolic time interval.

4. The system for providing treatment information using phonocardiogram according to claim 1, wherein the predetermined four treatment informations are to a first, second, third and fourth treatment information, and the above arithmetic section:

calculates the first treatment information when the systolic time interval exceeds the predetermined first reference value and the amplitude conversion ratio does not exceed the predetermined second reference value;

calculates the second treatment information when the systolic time interval exceeds the predetermined first reference value and the amplitude conversion ratio exceeds the predetermined second reference value;

calculates the third treatment information when the systolic time interval does not exceed the predetermined first reference value and the amplitude conversion ratio exceeds the predetermined second reference other value; and calculates the fourth treatment information when the systolic time interval does not exceed the predetermined first reference value and the amplitude conversion ratio does not exceed the predetermined second reference other value.

5. The system for providing treatment information using phonocardiogram according to claim 4, wherein the predetermined first reference value is 300 to 310 ms, and the predetermined second reference value is 15%.

6. The system for providing treatment information using phonocardiogram according to claim 1, wherein the heart sound receiving means is a microphone mounted in an esophagus stethoscope.

7. The system for providing treatment information using phonocardiogram according to claim 1, wherein the DSP module comprises a preamplifier for amplifying the heart sound received from the heart sound receiving means; and a filtering means for filtering the heart sounds amplified by the preamplifier.

8. The system for providing treatment information using phonocardiogram according to claim 7, wherein the filtering means comprise an analog to digital converter for converting the amplified heart sounds into a digital signal; and a band pass filter for band-pass filtering the converted digital signal.

9. The system for providing treatment information using phonocardiogram according to claim 8, wherein the band pass filter performs a band-pass filtering using a frequency band of 8 to 1000 Hz.

10. The system for providing treatment information using phonocardiogram according to claim 1, wherein the arithmetic section calculates the phonocardiogram through a Hilbert transform of the digital signals.

11. The system for providing treatment information using phonocardiogram according to claim 1, wherein the output section comprises:

a display unit capable of displaying the calculated treatment information by the arithmetic section; and a speaker capable of outputting the heart sounds received from the heart sound receiving means.

12. The system for providing treatment information using phonocardiogram according to claim 1, wherein the phonocardiogram calculated by the DSP module shows a change of time as an X-axis, and illustrates whether the frequency of the phonocardiogram deviates from a range of 320-340 Hz upon expiration or whether the frequency deviates from a range of 210-230 Hz upon expiration.

* * * * *

UNITED STATES PATENT AND TRADEMARK OFFICE
CERTIFICATE OF CORRECTION

PATENT NO.       : 9,636,080 B2
APPLICATION NO.  : 14/814951
DATED            : May 2, 2017
INVENTOR(S)      : Sung-Hoon Kim et al.

It is certified that error appears in the above-identified patent and that said Letters Patent is hereby corrected as shown below:

Column 15, Lines 27-28:
"exceeds the predetermined second reference other value; and" should read, --exceeds the predetermined second reference value; and--.

Column 15, Lines 32-33:
"does not exceed the predetermined second reference other value." should read, --does not exceed the predetermined second reference value.--.

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*